US010639232B2

(12) United States Patent
Giraud et al.

(10) Patent No.: US 10,639,232 B2
(45) Date of Patent: May 5, 2020

(54) MASSAGE DEVICE WITH MASSAGE HEAD EQUIPPED WITH TAPPING FINGER

(71) Applicant: SEB S.A., Ecully (FR)

(72) Inventors: Camille Giraud, Lyons (FR); Laurence Laranjeira, Moidieu Detourbe (FR); Franck Mandica, Francheville (FR)

(73) Assignee: SEB S.A., Ecully (FR)

( * ) Notice: Subject to any disclaimer, the term of this patent is extended or adjusted under 35 U.S.C. 154(b) by 891 days.

(21) Appl. No.: 15/029,675

(22) PCT Filed: Oct. 15, 2014

(86) PCT No.: PCT/FR2014/052633
§ 371 (c)(1),
(2) Date: Apr. 15, 2016

(87) PCT Pub. No.: WO2015/055956
PCT Pub. Date: Apr. 23, 2015

(65) Prior Publication Data
US 2016/0271009 A1 Sep. 22, 2016

(30) Foreign Application Priority Data
Oct. 17, 2013 (FR) ..................................... 13 60117

(51) Int. Cl.
A61H 23/00 (2006.01)
A61N 1/04 (2006.01)
A61N 5/06 (2006.01)

(52) U.S. Cl.
CPC ......... A61H 23/006 (2013.01); A61N 1/0412 (2013.01); A61N 5/062 (2013.01);
(Continued)

(58) Field of Classification Search
CPC .... A61H 23/00; A61H 23/004; A61H 23/006; A61H 2003/007
See application file for complete search history.

(56) References Cited

U.S. PATENT DOCUMENTS 3,626,934 A   12/1971   Andis
4,729,368 A    3/1988   Guitay
(Continued)

FOREIGN PATENT DOCUMENTS

EP   0666071 A1   8/1995
EP   1973510 B1   9/2010
FR   2589726 A1   5/1987

Primary Examiner — LaToya M Louis
(74) Attorney, Agent, or Firm — The Webb Law Firm

(57) ABSTRACT

Provided is a facial massage device including: a massage head (1) that includes: a bearing element (20) that is intended to be placed against the face and that defines a bearing surface (S), at least one massage finger (21), each including a working head (22) intended to come into contact with the face and each being mobile between: a retracted position (R) in which the working head (22) is located short of the bearing surface (S) towards the inside of the massage head (1), an extended position (E) in which the working head (22) is located beyond the bearing surface (S) towards the outside of the massage head (1), means (25) for manoeuvring each massage finger (21) designed to move each of the massage fingers (21) alternately between the extended position (E) and the retracted position (R) thereof, and a drive housing (2) that carries the massage head (1) and that includes an electric motor (6) that actuates drive means (7) designed to transmit the drive from the electric motor (6) to the manoeuvring means (25), wherein the drive housing (2) is located opposite the working heads, relative to the bearing element (20).

28 Claims, 5 Drawing Sheets

(52) U.S. Cl.
CPC .. *A61H 2023/002* (2013.01); *A61H 2201/105* (2013.01); *A61H 2205/022* (2013.01); *A61N 2005/0644* (2013.01)

(56) References Cited

U.S. PATENT DOCUMENTS

| | | | |
|---|---|---|---|
| 8,951,216 B2* | 2/2015 | Yoo | A61H 7/005 601/101 |
| 2005/0137504 A1* | 6/2005 | Yano | A61H 1/008 601/101 |
| 2005/0148906 A1* | 7/2005 | Skover | A61B 17/54 601/17 |
| 2009/0306561 A1* | 12/2009 | Naganuma | A61H 7/004 601/137 |
| 2010/0331745 A1* | 12/2010 | Yao | A61H 23/0254 601/101 |
| 2012/0253246 A1* | 10/2012 | Yamazaki | A61H 39/04 601/101 |
| 2013/0261516 A1 | 10/2013 | Cilea et al. | |

* cited by examiner

MASSAGE DEVICE WITH MASSAGE HEAD EQUIPPED WITH TAPPING FINGER

CROSS-REFERENCE TO RELATED APPLICATIONS

This application is the United States national phase of International Application No. PCT/FR2014/052633 filed Oct. 15, 2014, and claims priority to French Patent Application No. 1360117 filed Oct. 17, 2013, the disclosures of which are hereby incorporated in their entirety by reference.

FIELD OF THE INVENTION

The present invention relates to devices used for the treatment of skin, particularly that of the face. The device according the invention makes it possible to, at a minimum, massage the skin in order to improve its tone. The massage device according to the invention will have applications for individuals who seek to look after their appearance by recontouring, firming and rejuvenating their skin, particularly that of the face.

DESCRIPTION OF RELATED ART

Skin massage devices typically comprise a body equipped with motor drive means and a massage head that comprises massage elements configured to be actuated by the motor drive means, via a transmission mechanism. Known art includes patents or patent applications EP 0 666 071 A1, FR 2 589 726 A1, and EP 1 973 510 81.

In document EP 0 666 071 A 1, the massage device includes two blade-shaped elements that rotate in opposite directions such that as the blades are brought toward each other they fold the skin. In one embodiment, the massage device comprises a flexible cable element in the form of a loop, the extremities of which are rotated in opposite directions, allowing the looped portion to fold the skin.

U.S. Pat. No. 3,626,934 describes a skin massage device with two fingers that produce an alternating tapping pattern according to the axial position of each finger in relation to the skin. The system features fingers shaped like hammers with a large surface area and such that only one of two hammers comes into contact with the skin.

Such massage devices make it possible to perform a "rolling" or "tapping" massage. However, this is not the only type of massage that would ensure a rejuvenation and/or firming of the face of the skin, particularly as a need has emerged for a device capable of producing this type of tapping massage or rhythmic stimulation suitable for the smaller, sensitive, curved areas of the face. Accordingly, the object of this invention is to implement a massage device capable of producing a tapping massage in such a way as to most closely reproduce the motions of a professional esthetician and as reliably as possible a massage performed with the tapping of two fingers, all while realizing a tapping frequency and massage duration that would be difficult, or impossible to achieve with manual massage, and while avoiding unpleasant sensations when the massage device is applied to the skin, particularly to the skin of the face.

SUMMARY OF THE INVENTION

To achieve this objective, the invention relates to a massage device for the face comprising:
a massage head that includes:
on top of the support element, one or more massage fingers, each comprising a working head designed to come into contact with the face and moving between:
a retraction position in which the working head is positioned below the support surface toward the interior of the massage head,
an extension position in which the working head is positioned above the support surface toward the exterior of the massage head,
means of actuation for each massage finger adapted to move each of the massage fingers alternately between its extension and retraction positions,
a gearbox that supports the massage head and that comprises an electric motor that actuates the drive means adapted to transmit the movement of the electric motor to the means of actuation.

Such a massage device, through the tapping performed by the massage finger, makes it possible to stimulate blood circulation around the eyes to reduce dark circles and puffiness. The massage device may also be used to treat wrinkles and fine lines on the face, particularly at the nasolabial fold, by stimulating blood circulation hampered by the folding of skin where fine lines are present, to stimulate the metabolism, and in particular, to stimulate the production of the building blocks of the skin.

In a preferred embodiment of the invention, the massage head comprises at least two massage fingers.

The implementation of two, alternately mobile massage fingers makes it possible to reproduce the movements of tapping massage as performed using two fingers on one hand. The support surface makes it possible to precisely position the massage head in relation to the area to be massaged, particularly in that it imposes a distance between the working heads and the tapped area so as to prevent discomfort.

The regularity of force applied by the fingers over the entire treatment duration is improved by means of this support surface. In fact, a treatment may last 10 to 20 minutes, and the user, by applying the device by means of this support surface throughout the treatment, will experience less fatigue from holding the device, and will be able to position the device with more precision. Furthermore, the electric motor enables a massage frequency and duration that is impossible to achieve with manual massage. In addition, the motor and support surface together ensure the reproducibility of the resulting massage.

In one variation of the preferred embodiment, the means of actuation are adapted to coordinate the movement of the massage fingers such that when one of the massage fingers is in the extension position, the other is in the retraction position and vice versa.

In another characteristic of the invention, the gearbox is positioned opposite the working heads in relation to the support element and below the latter. Such a configuration makes the massage device particularly suitable for the purposes of providing a tapping massage to the areas of the cheekbones under the eyes.

[In yet another characteristic of the invention, the support element comprises a concave support surface. Such a shape enables the support element to follow the contour of the cheekbones when areas under the eyes are being massaged. The regularity of force applied by the fingers is thus further improved throughout the treatment.

In another characteristic of the invention, the support element comprises a flat support surface.

In one characteristic of the invention, the support element comprises a smooth surface. Such a smooth surface allows the massage head to move across the face while remaining in contact with the skin in such a way that the massage head slides across the skin while the massage fingers perform the tapping massage.

In another characteristic of the invention, the massage fingers extend at least partially beyond a hollow body that at least partially surrounds the means of actuation.

In another characteristic of the invention, the massage device is adapted to ensure that each massage finger operates with a frequency of displacement greater than or equal to 2.5 Hz. Such massage frequencies, which are difficult if not impossible to achieve with manual massage, ensure optimal stimulation and a sense of well-being, and also ensure comfortable, pain-free use.

In yet another characteristic of the invention, each working head has, between its retraction position and extension position, an amplitude of displacement ranging from 5 mm to 15 mm. Such an amplitude of displacement ensures a massage that is simultaneously efficient and pleasurable.

In one characteristic of the invention, each working head in its extension position protrudes in relation to the support surface a distance ranging from 2 mm to 10 mm. Such an extension enables an efficient massage without applying too much force to the skin at the moment of impact.

In another characteristic of the invention, each working head comprises a convex work surface. Such a work surface shape enables a comfortable massage in that not all of the skin will be uniformly in contact the entire surface of the working head such that the impact of the working head on the skin is not painful. Furthermore, the convex shape of each work surface makes it possible to reach very small areas and to see the impact of each working head on the skin.

In one alternative embodiment of the invention, each working head comprises a flat work surface. This alternative embodiment makes it possible to stimulate a larger area than is possible with a convex work surface, all while exerting an evenly-distributed pressure across the skin.

In one characteristic of the invention, each working head comprises a rigid work surface. Such a rigid surface makes it possible to transmit all of the massage energy to the skin. The work surface, or even working the working head itself may thus be made of a rigid polymeric material, for example. The work surface may also be made of metal. The work surface may also take the shape of a metal ball. Such a metal ball has the advantage of providing a sensation of coolness on contact with the skin. One alternative embodiment of a device in accordance with the invention may then comprise for each working head a flexible and detachable cap used to attach the metal ball thereby making it possible to modify the rigidity of the work surface.

In another characteristic of the invention, each working head comprises an elastically deformable work surface. The work surface may thus be made of an elastomer.

In one characteristic of the invention, the massage device comprises means of applying an electrical current comprising at least one electrode intended to come into contact with the skin, which is connected to a current and/or electrical voltage generation unit. The implementation of such an electrode enables the application of low currents to the skin, which induce electrophoretic or iontophoretic phenomena promoting the penetration of the active ingredients applied to the skin prior to and/or during the massage.

In one alternative embodiment of this characteristic, the support element supports or comprises at least one electrode.

In one alternative embodiment of this characteristic, at least one working head supports at least one electrode.

In one embodiment of the invention, the massage device comprises a means of diffusing light in the direction of the face. The implementation of such a means of diffusing light makes it possible to perform a phototherapy treatment and/or to activate the active ingredients applied to the skin prior to and/or during the massage.

In one characteristic of this embodiment, the means of diffusing light comprise at least one light source and at least one optical diffusion system comprising an output surface intended to be oriented toward the face.

In one alternative embodiment of this characteristic, the support element comprises a light output surface.

In another alternative embodiment of this characteristic, the one or more working heads comprise a light output surface.

In another embodiment of the invention, the massage device comprises a means of applying or dispensing a cosmetic product. The implementation of such a means of application makes it possible to dispense onto the skin a cosmetic product prior to and/or during the massage.

In one characteristic of this embodiment, the means of applying or dispensing cosmetic product comprise at least one cap comprising a pad moistened with a cosmetic product, which is detachably mounted on a massage finger.

In another characteristic of this embodiment, the means of applying or dispensing cosmetic product comprise a reservoir for a cosmetic product and at least one dispensing nozzle connected to a system to extract the product in the reservoir, for example, a pump.

In one alternative embodiment of this characteristic, the means of applying or dispensing cosmetic product comprise at least one dispensing nozzle positioned in a working head or in the support element.

In one characteristic of the invention, the massage head is detachably mounted on the gearbox. The detachable nature of the massage head makes it possible to use multiple massage heads interchangeably with the same gearbox.

In one alternative embodiment of this characteristic, the massage head comprises means of identification and the gearbox comprises means of recognition for the means of identification associated with a control unit designed to control the operation of the device according to the recognized massage head. The implementation of such an identification system makes it possible to automate control of the massage device such that the user is not required to do so.

Of course, the various characteristics, variations and embodiments of the invention may be combined with each other in various combinations to the extent that they are not incompatible or mutually exclusive.

BRIEF DESCRIPTION OF THE DRAWINGS

Furthermore, various other characteristics of the invention will become evident in the annexed description with reference to the illustrations of non-exhaustive embodiments of a massage device according to the invention.

Figure 1:
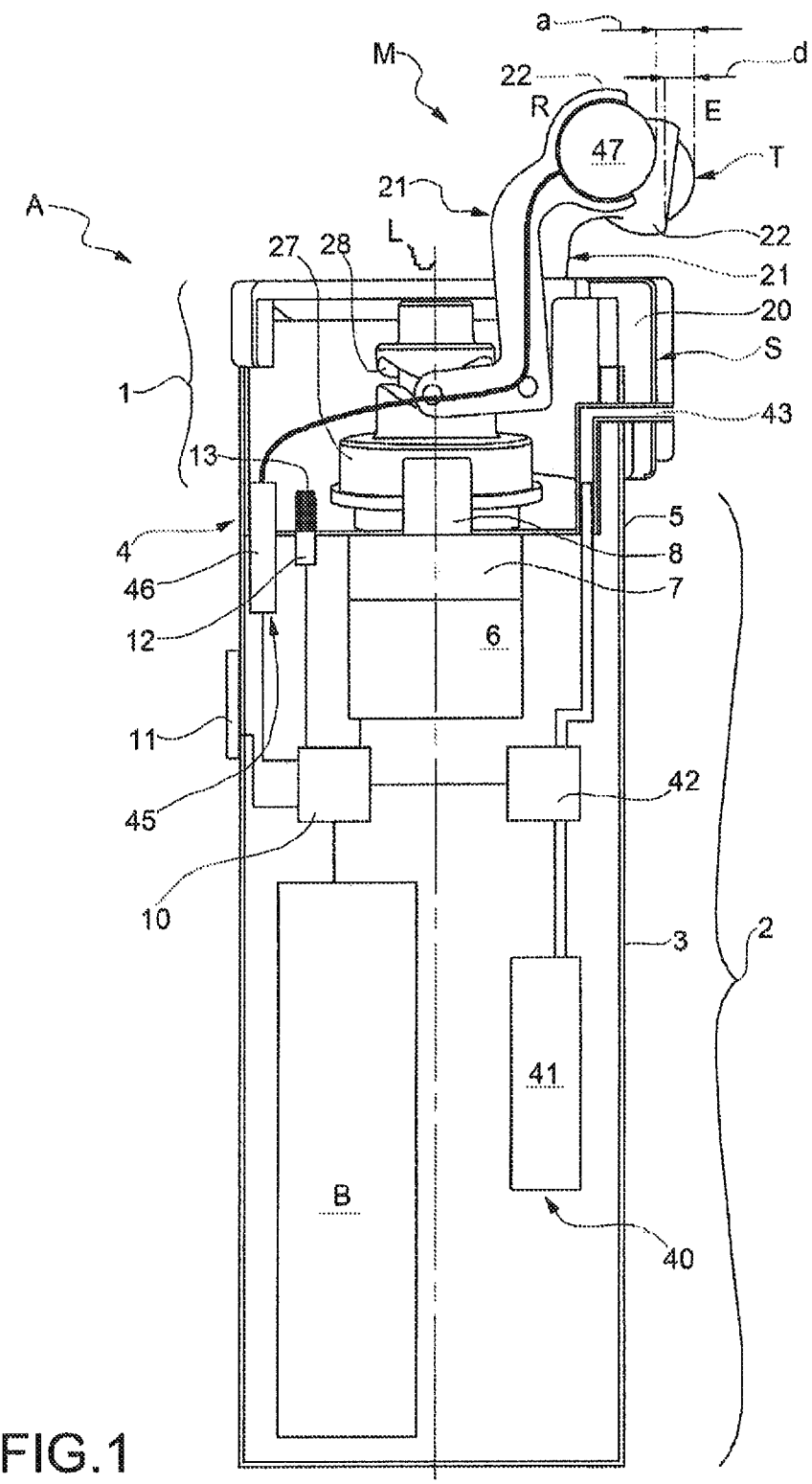
FIG. 1 is a schematic cross-sectional view of a massage device according to the invention.

Figure two is a perspective view of the detachable massage head fitted on the massage device in FIG. 1.

Figure 2:
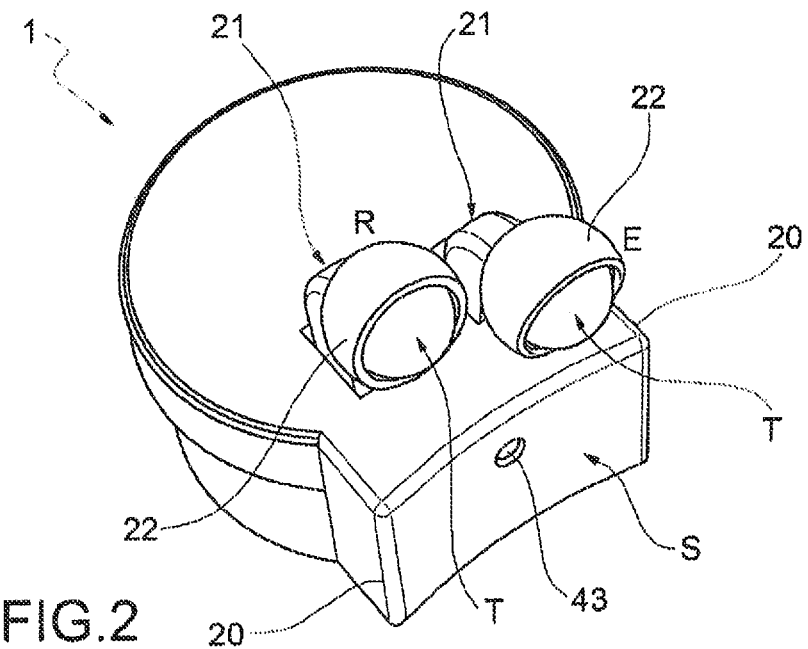
Figure 3:
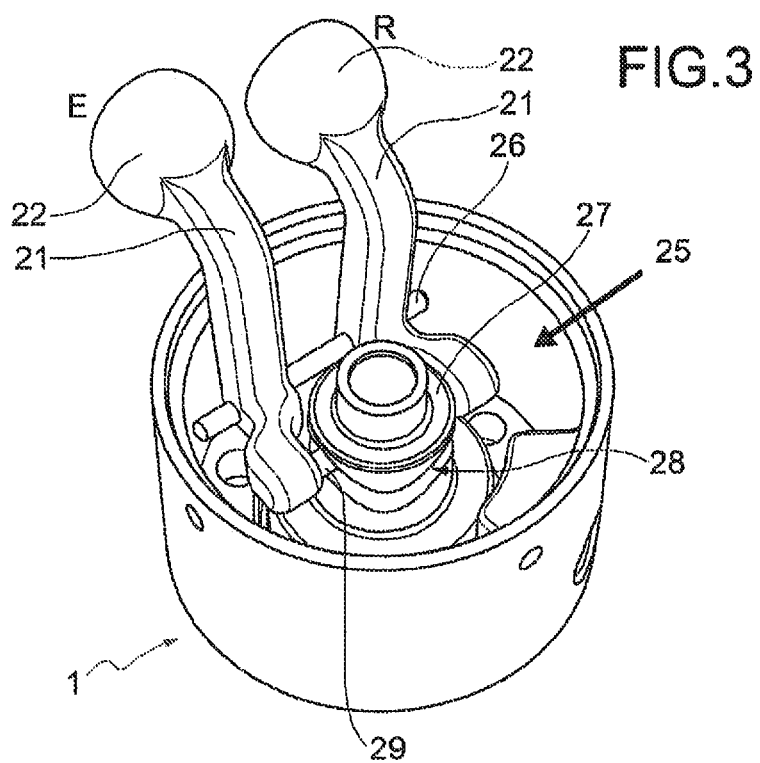

FIG. 3 is a partially cutaway perspective view of the massage head illustrated in FIG. 2.

Figure 4:
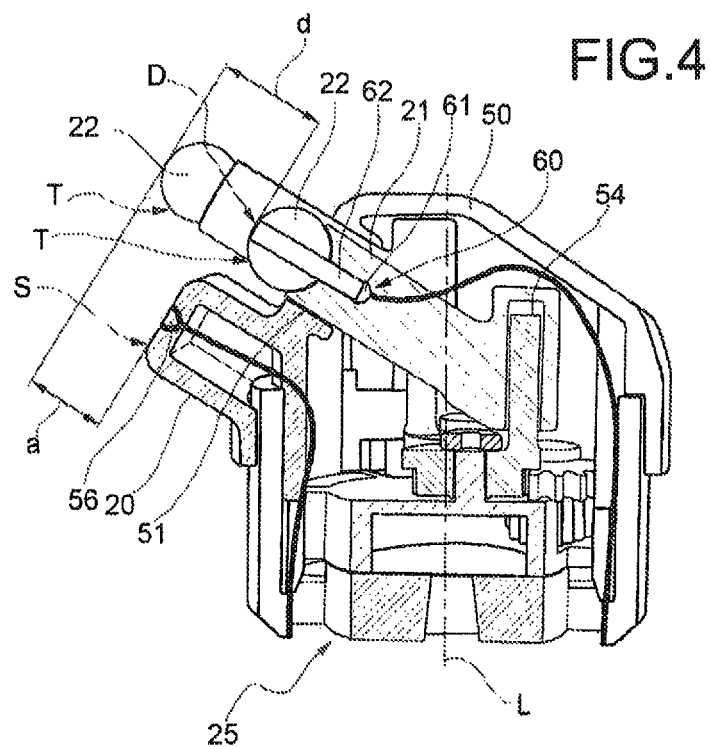

FIG. 4 is a schematic cross-sectional view of another embodiment of a detachable massage head for a massage device according to the invention.

Figure 5:
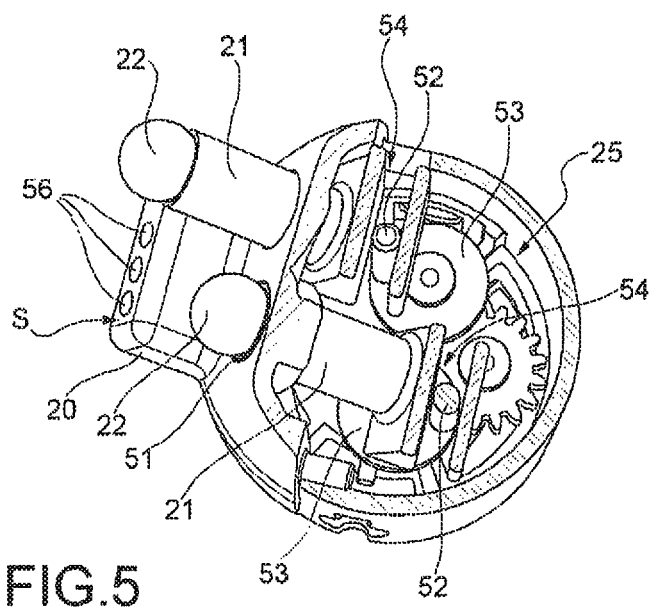

FIG. 5 is a partially cutaway perspective view of the massage head illustrated in FIG. 4.

Figure 6:
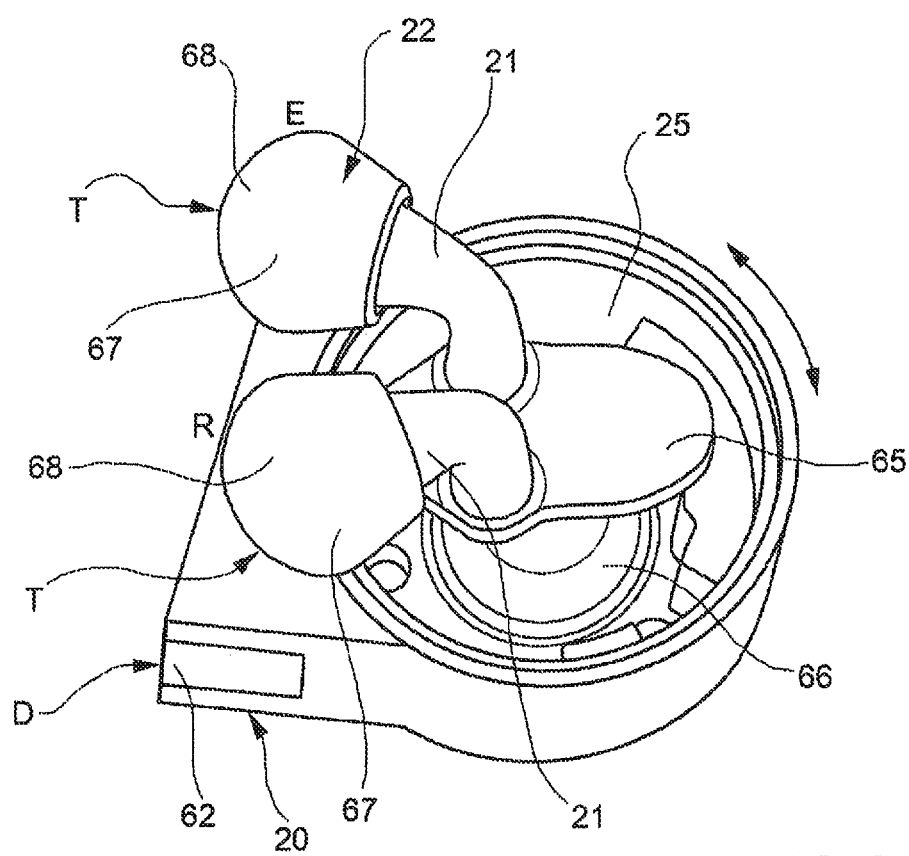

FIG. 6 is a partially cutaway perspective view of another embodiment of a detachable massage head for a massage device according to the invention.

Figure 7:
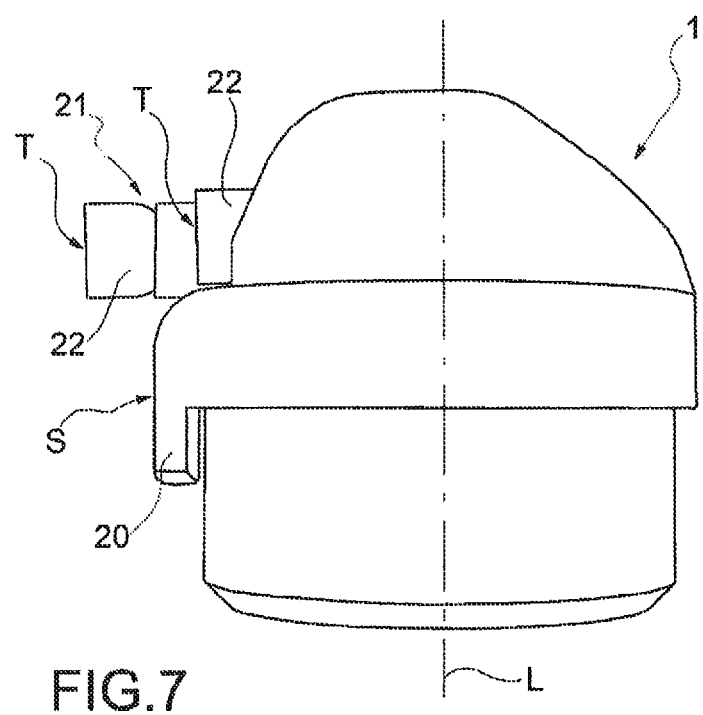

FIG. 7 is an elevated schematic side view of another embodiment of a detachable massage head for a massage device according to the invention.

DETAILED DESCRIPTION OF THE INVENTION

It should be noted that for these figures, the structural and/or functional elements common to distinct variations may be identified by the same references.

A massage device according to the invention, as illustrated in FIG. 1 and illustrated in its entirety by reference A, consists of a massage head (1) designed to be detachably mounted on a gearbox (2). The massage head (1) is designed to exert mechanical action on the skin of the user's face via the massage elements (M) powered by an electric motor.

To this effect, the gearbox (2) comprises a long and generally cylindrical body (3) comprising at one end (4) a means of adaptation (5) on which the massage head (1) can be detachably mounted. The means of adaptation (5) are, as in the example depicted, formed by a sheath inside which the massage head (1) is partially engaged.

The gearbox (2) comprises, inside the body (3), an electric motor (6) that actuates the drive means (7) adapted to transmit the movement of the electric motor to the massage elements of the massage head (1). According to the example depicted, the drive means (7) comprises a reducer (not shown) that drives an output shaft (8) accessible at the level of the gearbox (2) means of adaptation (5).

The electric motor (6) is driven by a control unit (10) powered by a battery pack (B) positioned inside the body (3). Of course, the power supply to the control unit (10) may also be obtained directly from an electric circuit by way of a transformer. The control unit (10) is also connected to a manual control interface (11) accessible on the exterior of the body (3). The manual control interface (11) may, for example, comprise an on-off switch and/or means for the manual selection of operating programs.

The gearbox (2) also comprises means of recognition (12) connected to a control unit (10) designed to read the means of identification (13) on the massage head (1).

The control unit (10) is thus designed to control the operation of the massage device (A) with respect to the massage head (1) recognized via the means of identification (13). The control of the operation of the massage device (A) may notably consist of a determination of the rotation speed of the electric motor (6) such that the speed is adapted for massage prior to being performed by the massage elements (M). The means of identification (13) may, for example, comprise an RFID chip whereas the means of recognition (12) may be adapted to read such an RFID chip. Of course, the means of identification (13) and of recognition (12) will be implemented in any other appropriate manner, for example, using a mechanical contact or electrical identification system, or even a magnetic identification system using permanent magnets and reed switches.

According to the invention, the massage head (1) is designed to perform a massage by tapping. To this effect, the massage head (1) comprises, as illustrated in FIG. 2, a support element (20) designed to come into contact with the face to delimit a work area. Accordingly, the support element (20) defines a support surface (S) that forms a reference surface. As illustrated in the figures and as evident to experts in the art, the support element (20) is positioned on the outside of the vertical wall of the housing, such that the support surface (S) is logically parallel to the longitudinal axis (L) of the gearbox.

According to the example depicted, the support surface (S) is smooth and concave in shape, which allows it to match the contour of the cheekbones when the massage is performed in the area under or surrounding the eyes.

The massage head (1) comprises above the support surface (S) and opposite the gearbox (2) in relation to said support surface (S), the massage elements (M) that comprise at least two massage fingers (21) that each comprise one working head (22) designed to come into contact with the face.

The two massage fingers (21) are each mobile between, firstly, a retraction position (R) corresponding to the position of the massage finger (21) in the foreground of FIG. 1, and secondly, an extension position (E), corresponding to the position of the massage finger (21) in the background of FIG. 1.

In the retraction position (R) the working head (22) of each massage finger (21) is below the support surface (S) toward the interior of the massage head (1). In the extension position (E) the working head (22) of each massage finger (21) is above the support surface (S) toward the exterior of the massage head (1). Each working head (22) has, between its retraction position (R) and extension position (E), an amplitude of displacement (a) ranging from 5 mm to 15 mm. Furthermore, in the extension position (E) each working head (22) protrudes in relation to the support surface (S) by a distance (d) ranging from 2 mm to 10 mm.

The massage head (1) also comprises means of actuation (25) adapted to alternately displace each of the massage fingers (21) between its extension position (E) and retraction position (R). The means of actuation (25) are thus adapted to cooperate with the drive means (7) and in particular with the output shaft (8) so as to transmit and transform the rotational movement of the electric motor (6) into the alternating movement of the massage fingers (21).

According to the example depicted, each massage finger (21) has a generally "S" shaped form and is supported by a hinge pin (26) located in the lower half of the massage finger (21) while the top half of the same massage finger (21) holds the working head (22). The means of actuation therefore comprise a cam (27) that can rotate on its own axis in a direction perpendicular to the hinge pin (26) and coaxial to the output shaft (8). The cam (27) therefore has, on its lower surface, a housing for the output shaft (8). The cam (27) comprises, in part, a cam track (28) around its periphery, which on the prototype is sinusoidal in shape.

Each massage finger has, at a certain distance from the hinge pin (26) a cam follower (29) engaged in the cam track (28) such that the rotation of the cam (27) on its own axis induces a reciprocal movement of each cam follower (29). With respect to the contour of the massage fingers (21) the reciprocal movement of each cam follower (29) induces a reciprocal oscillation of the massage fingers in rotation around the hinge pin (26).

Preferentially, the massage device (A) and, more specifically, the means of actuation (25), drive means (7) and the control unit (10) are each adapted to supply each massage finger with a frequency of displacement greater than or equal to 2.5 Hz.

It should be noted that, according to the example depicted, the means of actuation (25) are adapted to coordinate the movement of the massage fingers (21) such that when one of the massage fingers (21) is in the extension position (E), the other massage finger (21) is in the retraction position (R) and vice versa.

The massage device thus created is implemented in the following manner. The support surface (S) is placed against the skin, then the user switches on the massage device (A) using the interface (11), the massage fingers (21) are driven to an oscillating movement that mimics the movements of a massage performed with two fingers, for example, the index and middle fingers, tapping alternately on the skin of the face, particularly in the area around the eyes.

According to the example depicted, and so as to best mimic the movement of fingers, each working head comprises a work surface (T) that is convex in shape and that in this instance is both spherical and rigid.

The massage performed with the device according to the invention has the effect of stimulating, smoothing, relaxing, and notably, reducing dark circles and puffiness of the skin under the eyes, filling out fine lines and wrinkles. To optimize the treatment, the massage device (A) as depicted in FIGS. 1 to 3 comprises a means of applying or dispensing a cosmetic product (40).

According to the example depicted, the means of applying or dispensing cosmetic products (40) comprise a reservoir (41) positioned inside the gearbox (2) and connected, via a system of conveyance (42), such as a pump (42), to a dispensing nozzle (43) positioned in the support element (20). The pump is operated with the control unit (10) so as to control the dispensing of the cosmetic product while the massage device (A) is in operation. Of course, one or both of the working heads could comprise a nozzle for the dispensing of cosmetic products.

Furthermore, and as always according to the example depicted in FIGS. 1 to 3, the massage device (A) also comprises means of applying an electrical current (45) to the skin, which consists of a current and/or electrical voltage generation unit (46). The generation unit (46) is controlled via the control unit (10). The generation unit (46) is connected to an electrode (47) positioned on a working head (22).

When the massage device (A) is in use, the control unit (10) controls the operation of the generation unit (46) such that when the electrode (47) is in contact with the skin, electrophoretic phenomena are induced to promote the absorption of active ingredients contained in the cosmetic product.

According to the invention, the massage fingers (21) are not limited to an oscillating movement around a horizontal axis. Accordingly, FIGS. 4 and 5 depict a massage head (1) for a device according to the invention, the massage fingers (21) of which have distinct kinematics.

In this example, each massage finger (21) is formed as a rectilinear piston that at least partially extends outside of a hollow body (50) that surrounds the means of actuation (25). Each finger is thus guided through a translational movement through a bore (51) fitted in the hollow body (50).

The extremity of each massage finger (21) inside the hollow body (50) engages with an eccentric rod (52) driven by an actuating sheave (53) that is a component of the means of actuation (25). The eccentric rod (52) is positioned in a chamber (54) that is rigidly connected to its corresponding massage finger and in which the eccentric rod (52) moves translationally such that its rotation with the actuating sheave (53) is transformed into a translational movement of the corresponding massage finger (21).

In addition, according to this example embodiment, the support surface (S) is flat.

Continuing to reference the example embodiment, the path traveled by the massage fingers is not perpendicular to the longitudinal axis (L) of the gearbox, but rather forms a non-zero angle with the latter, which in the example depicted measures approximately 30°. This construction method is advantageous in that it allows the user to easily access narrow areas of the face, such as areas immediately surrounding the eyes or mouth, without interference from the body of the device.

Furthermore, in the example embodiment, the support element (20) supports electrodes (56) through which an electrical current is transmitted to the skin.

Continuing to reference the example embodiment, the massage head comprises a means of diffusing light in the direction of the face (60). In this case, the means of diffusion (60) are housed in a massage finger (21) and comprise a light source (61) such as a light-emitting diode operated via the control unit (10). The light source (61) is thereby connected to an optical system (62) comprising an output surface (D) positioned on the work surface (T) and thus intended to be oriented toward the face of the user operating the massage device (A) according to the invention.

FIG. 6 illustrates yet another embodiment of a massage head (1) for a massage device according to the invention. In this embodiment, the two massage fingers (21) are driven by the same deck (65) that oscillates in rotation around a vertical axis that in turn is driven, via a bore underneath the deck, by an eccentric sheave (66) that is a component of the means of actuation (25) for which the rod runs through the bore to the deck. According to this example embodiment, each massage finger (21) supports a detachable cap (67) forming the corresponding working head (22).

In another example embodiment, this cap could be made of a flexible, elastomer-type material.

In another embodiment, it could comprise a pad (68) moistened with a cosmetic product forming the work surface (T). The detachable caps (67) thus form the means of applying or dispensing cosmetic product.

In this example embodiment, the support element (20) comprises an optical system (62) to diffuse the light produced by a light source located either in the massage head (1) or in the gearbox (2).

FIG. 7 illustrates a variation of the embodiment of the massage head illustrated in FIGS. 4 and 5, with which the massage fingers (21) have equivalent kinematics. This embodiment differs from the massage head illustrated in FIGS. 4 and 5 in that the massage fingers move in alternate translation perpendicularly to the longitudinal axis (L) of the gearbox. In addition, in this embodiment, the work surface (T) of each massage finger is flat.

Of course, various other modifications or variations of the device and the massage head according to the invention may be envisioned within the framework of the annexed claims.

The invention claimed is:

1. A massage device for the face comprising:
   a massage head that comprises:
   a support element designed to come into contact with the face and that defines a support surface (S),
   one or more massage fingers, each comprising a working head designed to come into contact with the face and moving between:
   a retraction position (R) in which the working head is positioned below the support surface (S) toward an interior of the massage head,
   an extension position (E) in which the working head is positioned above the support surface (S) toward an exterior of the massage head, means of actuation for each massage finger adapted to move each massage finger between its extension position (E) and retraction position (R) alternately, and a gearbox that supports the massage head and that comprises an electric motor that actuates a drive means adapted to transmit movement of the electric motor to the means of actuation, wherein the gearbox is positioned opposite the working heads in relation to the support element, and wherein the support surface of the support element is positioned between the working heads and the gearbox in the retraction position and the extension position of the working heads.

2. The massage device as in claim 1, wherein the massage head comprises at least two massage fingers.

3. The massage device as in claim 2, wherein the means of actuation are adapted to coordinate the movement of massage fingers such that when one massage finger is in the extension position (E), the other is in the retraction position (R) and vice versa.

4. The massage device as in claim 1, wherein the support element comprises a concave support surface (S).

5. The massage device as in claim 1, wherein the support element comprises a flat support surface (S).

6. The massage device as in claim 1, wherein the support element comprises a smooth support surface (S).

7. The massage device as in claim 1, wherein the massage fingers at least partially extend out of a hollow body that at least partially surrounds the means of actuation.

8. The massage device as in claim 1, wherein the device is adapted to ensure a frequency of displacement for each of the massage fingers of greater than or equal to 2.5 Hz.

9. The massage device as in claim 1, wherein each working head has, between its retraction position (R) and extension position (E), an amplitude of displacement (a) ranging from 5 mm to 15 mm.

10. The massage device as in claim 1, wherein the extension position (E) of each working head protrudes in relation to the support surface (S) by a distance (d) ranging from 2 mm to 10 mm.

11. The massage device as in claim 1, wherein each working head comprises a convex work surface (T).

12. The massage device as in claim 1, wherein each working head comprises a flat work surface (T).

13. The massage device as in claim 1, wherein each working head comprises a hard work surface (T).

14. The massage device as in claim 1, wherein each working head comprises a metal work surface (T).

15. The massage device as in claim 1, wherein each working head comprises an elastically deformable work surface (T).

16. The massage device as in claim 1, wherein the device comprises means of applying an electrical current comprising at least one electrode destined to come into contact with a user's skin and that is connected to an electrical current and/or voltage generation unit.

17. The massage device as in claim 16, wherein the support element holds or comprises at least one electrode.

18. The massage device as in claim 16, wherein at least one working head holds at least one electrode.

19. The massage device as in claim 1, wherein the device comprises a means of diffusing light in a direction of the face.

20. The massage device as in claim 19, wherein the means of diffusing light comprise at least one light source and at least one optical diffusion system comprising an output surface (D) intended to be oriented toward the face.

21. The massage device as in claim 20, wherein the support element comprises a light output surface (D).

22. The massage device as in claim 20, wherein at least one of the working heads comprises a light output surface (D).

23. The massage device as in claim 1, wherein the device comprises means of applying or dispensing a cosmetic product.

24. The massage device as in claim 23, wherein the means of applying or dispensing a cosmetic product comprise at least one cap comprising a pad moistened with a cosmetic product and that is detachably mounted on a massage finger.

25. The massage device as in claim 23, wherein the means of applying or dispensing comprise a reservoir for a cosmetic product and at least one dispensing nozzle connected to an extraction system for the product in the reservoir.

26. The massage device as in claim 25, wherein the means of applying or dispensing comprise at least one dispensing nozzle located in a working head or in the support element.

27. The massage device as in claim 1, wherein the massage head is detachably mounted on the gearbox.

28. The massage device as in claim 27, wherein the massage head comprises means of identification and wherein the gearbox comprises means of recognition for the means of identification associated with a control unit designed to control the operation of the massage device according to an identified massage head.

* * * * *